US006677256B1

(12) United States Patent
Sun et al.

(10) Patent No.: US 6,677,256 B1
(45) Date of Patent: *Jan. 13, 2004

(54) FIBROUS MATERIALS CONTAINING ACTIVATING AGENTS FOR MAKING SUPERABSORBENT POLYMERS

(75) Inventors: Tong Sun, Neenah, WI (US); Werner Lonsky, Appleton, WI (US); Yong Li, Appleton, WI (US); Jian Qin, Appleton, WI (US); Xiaomin Zhang, Appleton, WI (US); Jacek Dutkiewicz, Cordova, TN (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/473,183

(22) Filed: Dec. 28, 1999

(51) Int. Cl.[7] .............................. B32B 9/04; B32B 5/02; B32B 23/02; A61F 13/15
(52) U.S. Cl. ....................... 442/153; 442/154; 442/165; 442/414; 604/367; 604/374; 604/375
(58) Field of Search ................................ 442/153, 154, 442/158, 165, 408, 414; 428/361, 375; 604/367, 374, 375

(56) References Cited

U.S. PATENT DOCUMENTS

| | | | |
|---|---|---|---|
| 2,539,704 A | 1/1951 | Schoene et al. ............. 260/231 |
| 2,827,452 A | 3/1958 | Schlenk et al. ............. 260/209 |
| 2,856,307 A | 10/1958 | Fredrickson ................ 106/208 |
| 2,917,506 A | 12/1959 | Caldwell et al. ............ 260/234 |
| 3,061,444 A | 10/1962 | Rogers et al. ................. 99/140 |
| 3,140,184 A | 7/1964 | Robbins ......................... 99/28 |
| 3,210,375 A | 10/1965 | Porret et al. ............. 260/340.7 |
| 3,222,358 A | 12/1965 | Touey et al. ................. 260/209 |
| 3,225,028 A | 12/1965 | Nordgren ..................... 260/209 |
| 3,346,555 A | 10/1967 | Nordgren ..................... 260/209 |
| 3,453,258 A | 7/1969 | Parmerter et al. .......... 260/209 |
| 3,553,191 A | 1/1971 | Parmerter et al. .......... 260/209 |
| 3,998,690 A | 12/1976 | Lyness et al. |
| 4,144,122 A | 3/1979 | Emanuelsson et al. ...... 162/158 |
| 4,357,468 A | 11/1982 | Szejtli et al. ................. 536/56 |
| 4,431,481 A | 2/1984 | Drach et al. |
| 4,548,847 A | * 10/1985 | Aberson et al. ............... 428/74 |
| 4,820,307 A | 4/1989 | Welch et al. |
| 4,889,597 A | 12/1989 | Bourbon et al. |
| 5,098,793 A | 3/1992 | Rohrbach et al. ........... 428/532 |
| 5,134,127 A | 7/1992 | Stella et al. ................... 514/58 |
| 5,139,687 A | 8/1992 | Borgher, Sr. et al. ........ 252/8.6 |
| 5,188,064 A | 2/1993 | House ......................... 119/172 |
| 5,207,830 A | 5/1993 | Cowan et al. ............... 106/672 |
| 5,234,610 A | 8/1993 | Gardlik et al. ................ 252/8.6 |
| 5,238,682 A | 8/1993 | Akasaka et al. ............. 424/409 |
| 5,348,667 A | 9/1994 | Bacon et al. .................. 252/8.6 |
| 5,399,240 A | 3/1995 | Graef et al. |
| 5,429,628 A | 7/1995 | Trinh et al. .................. 604/359 |
| 5,474,689 A | 12/1995 | Laughlin et al. .............. 252/8.8 |
| 5,505,718 A | 4/1996 | Roe et al. .................... 604/368 |
| 5,534,165 A | 7/1996 | Piosof et al. ................ 252/8.91 |
| 5,578,563 A | 11/1996 | Trinh et al. .................. 510/513 |
| 5,672,418 A | 9/1997 | Hansen et al. |
| 5,714,445 A | 2/1998 | Trinh et al. .................. 510/103 |
| 5,718,728 A | 2/1998 | Arkens et al. ................ 8/116.1 |
| 5,728,823 A | 3/1998 | Reuscher et al. ............. 536/46 |
| 5,776,842 A | 7/1998 | Wood et al. ................. 442/394 |
| 5,782,963 A | 7/1998 | Nohr et al. ............... 106/31.27 |
| 5,804,605 A | 9/1998 | Palumbo ....................... 521/28 |
| 5,830,835 A | 11/1998 | Severns et al. ............. 510/102 |
| 5,837,627 A | 11/1998 | Halabisky et al. |
| 5,843,063 A | 12/1998 | Anderson et al. ........... 604/378 |
| 5,858,021 A | 1/1999 | Sun et al. ...................... 8/125 |
| 5,871,719 A | 2/1999 | Lucas et al. ................... 424/65 |
| 5,942,217 A | 8/1999 | Woo et al. .................. 424/76.1 |
| 6,241,853 B1 | 6/2001 | Smith et al. |
| 6,287,679 B1 | * 9/2001 | Pappas et al. ............ 428/304.4 |

FOREIGN PATENT DOCUMENTS

| | | |
|---|---|---|
| EP | 0 483 380 | 11/1991 |
| EP | 0 419 434 | 5/1993 |
| WO | WO 91/05108 A1 | 4/1991 |
| WO | WO 94/14888 | 7/1994 |
| WO | WO 91/05108 | 4/1997 |
| WO | WO 98/22061 | 5/1998 |
| WO | WO 98/24832 * | 6/1998 |
| WO | WO 98/30387 B1 | 7/1998 |
| WO | WO 98/42286 | 10/1998 |
| WO | WO 99/31312 B1 | 6/1999 |

OTHER PUBLICATIONS

Xu, G.G., et al., "*Effects of Poly(vinyl Alcohol) on the Strength of Kraft Paper Crosslinked by a Polycarboxylic Acid*", Journal of Pulp and Paper Science, vol. 27, No. 1, Jan. 2001, pp. 14–17.

Xu, Yufeng, et al. "*Application of Polymeric Multifunctional Carboxylic Acids to Improve Wet Strength*", TAPPI Journal vol. 81, 1998, vol. 81, No. 11, Nov., 1998, pp. 159–164.

Yang, Charles Q., et al. "*Polymers of Maleic Acid as Nonformaldehyde Wrinkle Free Finishing Agents*", Book of Papers, 1996 International Conference & Exhibition, American Association of Textile Chemists and Colorists, Sep. 15–18, 1996, pp. 160–164.

* cited by examiner

Primary Examiner—Cheryl A. Juska
Assistant Examiner—Jenna-Leigh Befumo
(74) Attorney, Agent, or Firm—John S. Pratt; Patricia A. Charlier

(57) ABSTRACT

Absorbent structures that form superabsorbent polymers in situ. The structures include an absorbent material and a fibrous material containing an activating agent. The fibrous material releases the activating agent upon stimulation with an activator, which causes the polymer to become a superabsorbent polymer. The absorbent component is desirably a water-swellable, water-insoluble polymer. The absorbent structures form a superabsorbent composition in situ. Methods of making the activating agent containing fibrous material are provided.

18 Claims, No Drawings

FIBROUS MATERIALS CONTAINING ACTIVATING AGENTS FOR MAKING SUPERABSORBENT POLYMERS

FIELD OF THE INVENTION

The present invention generally relates to an absorbent structure that forms a superabsorbent composition in situ having the ability to absorb a large quantity of liquid. The structure includes an absorbent material and a fibrous material having an activating agent incorporated therein. The fibrous material releases the activating agent in response to contact with liquid and the activating agent activates the absorbent material so that it becomes a superabsorbent material. The absorbent structure is useful in disposable absorbent products, such as those disposable absorbent products that are used to absorb bodily fluids.

BACKGROUND OF THE INVENTION

The use of water-swellable, generally water-insoluble absorbent materials, commonly known as superabsorbents, in disposable absorbent personal care products is known. Such absorbent materials are generally employed in absorbent products such as diapers, training pants, adult incontinence products, and feminine care products in order to increase the absorbent capacity of such products while reducing their overall bulk. Such absorbent materials are generally present in absorbent products in a fibrous matrix, such as a matrix of wood pulp fluff. A matrix of wood pulp fluff generally has an absorbent capacity of about 6 grams of liquid per gram of fluff. The superabsorbent materials generally have an absorbent capacity of at least about 10, desirably of about 20, and often of up to about 1000 times their weight in water. Clearly, incorporation of such absorbent materials in personal care products can reduce the overall bulk while increasing the absorbent capacity of such products.

A wide variety of materials have been described for use as absorbent materials in personal care products. Such materials include natural-based materials such as agar, pectin, gums, carboxyalkyl starch, and carboxyalkyl cellulose, as well as synthetic materials such as polyacrylates, polyacrylamides, and hydrolyzed polyacrylonitrile. While such natural-based absorbent materials are known for use in personal care products, they have not gained wide usage in such products, at least in part because their absorbent properties are generally inferior compared to the synthetic absorbent materials, such as the sodium polyacrylates. Specifically, many of the natural-based materials tend to form soft, gelatinous masses when swollen with a liquid. When employed in absorbent products, the presence of such soft gelatinous masses tends to prevent the transport of liquid within the fibrous matrix in which the absorbent materials are incorporated. This phenomenon is known as gel blocking. Once gel blocking occurs, the product cannot efficiently absorb subsequent insults of liquid, and the product tends to leak. Further, many of the natural-based materials exhibit poor absorption properties, particularly when subjected to external pressures.

In contrast, synthetic absorbent materials are often capable of absorbing large quantities of liquid while maintaining a generally stiff, non-mucilaginous character. Accordingly, synthetic absorbent materials can be incorporated in absorbent products while minimizing the likelihood of gel blocking.

One property of currently available superabsorbent materials is that such materials typically very rapidly absorb the liquid that comes into contact with the superabsorbent material. While such quick absorbency of the liquid may be desirable in many applications, there are certain applications in which it is not desirable. For example, in an absorbent structure that is insulted with a liquid at only a very localized location, it would generally be desirable to have the liquid distributed throughout the entire volume of the absorbent structure so that the absorbent capacity of the entire absorbent structure is utilized. However, if the superabsorbent material located near the localized insult location absorbs the liquid very quickly, this superabsorbent material may swell and restrict the flow of the liquid throughout the rest of the absorbent structure, possibly resulting in the liquid leaking out of the absorbent structure in the area of the localized insult location. Accordingly, it is often desirable to employ a superabsorbent material in the localized insult location that actually absorbs the liquid at a slow rate. This allows the liquid to be distributed throughout the absorbent structure first and then be subsequently absorbed by the superabsorbent material.

Several methods are known to slow down the liquid absorbing rate of a relatively fast absorbing superabsorbent material. For example, it is possible to coat the fast absorbing superabsorbent material with a material that is nonabsorbent and/or hydrophobic. Such coating materials tend to temporarily shield the underlying superabsorbent material from any liquid and, thus, delay the absorption of the liquid by the superabsorbent material. However, such coating materials often reduce the overall liquid capacity of the superabsorbent material, add to the expense and complexity of preparing the superabsorbent material, and may negatively affect other liquid handling properties of the superabsorbent material.

Commercially available superabsorbents are generally in a substantially neutralized or salt form. This is because, in general, in order to have a relatively high capacity for liquid absorption, a water-swellable, water-insoluble polymer must be a polyelectrolyte. However, such superabsorbents absorb liquid relatively quickly, leading to the above discussed problems. It is known that when an acidic or basic water-swellable, water-insoluble polymer, substantially in its free acid or free base form, respectively, is mixed with a basic second material or an acidic second material, respectively, the resulting absorbent composition will exhibit both a relatively high capacity for liquid absorption as well as a relatively slow liquid absorbing rate. This is believed to be because, as the mixture is placed in an aqueous solution, the acidic or basic water-swellable, water-insoluble polymer, substantially in its free acid or free base form, respectively, reacts with the basic second material or the acidic second material, respectively, and the chemical equilibrium is in favor of converting the acidic or basic water-swellable, water-insoluble polymer from its free acid or free base form, respectively, to its respective salt form. As such, the mixture comprising the converted water-swellable, water-insoluble polymer will now exhibit a relatively high capacity for liquid absorption. However, because the conversion of the water-swellable, water-insoluble polymer, from its free acid or free base form, respectively, to its respective salt form is a relatively slow process of ionization and ion diffusion into the polymer, the water-swellable, water-insoluble polymer will also exhibit a relatively slow liquid absorbing rate. In addition, the conversion of the water-swellable, water-insoluble polymer from its free acid or free base form to its respective salt form in an electrolyte-containing solution, such as an aqueous sodium chloride solution, has a substantial desalting effect on the electrolyte-containing solution, thereby improving the liquid-absorbing performance of the mixture by alleviating the salt-poisoning effect.

WO 98/24832 discloses an absorbent composition that includes a polymeric absorbent material and a second material. The two components are mixed and used in an absorbent article, desirably in conjunction with a fibrous matrix. The second material can be provided in the form of particles, flakes, fibers, films, and nonwoven structures or the two components can be provided as a bi-component fiber. This composition has disadvantages in terms of handling properties and structural integrity.

A single material or polymer comprising both acidic and basic functional groups within its molecular structure will not exhibit the desired absorbent properties described above. This is believed to be because such acidic and basic functional groups within a single molecular structure will typically react with each other and might result in an over-crosslinked polymer structure. As such, it generally is not possible to prepare an absorbent composition by preparing a copolymer from acidic and basic monomers or by preparing a molecular level dispersion, such as in an aqueous solution, of water-soluble acidic and basic materials since during such copolymerization or molecular level dispersion the acidic and basic materials will typically react with each other and crosslink.

Accordingly, it is an object of the present invention to provide a fibrous matrix that releases an activating agent upon contact with an insult liquid, wherein the activating agent causes an absorbent material to form a superabsorbent polymer.

It is also an object of the present invention to provide an absorbent structure that will form a superabsorbent polymer in situ upon contact with a liquid to be absorbed.

SUMMARY OF THE INVENTION

The present invention is directed to absorbent structures that form superabsorbent polymers in situ. The structures include an absorbent material and a fibrous material containing an activating agent. The fibrous material releases the activating agent, which causes the polymer to become a superabsorbent polymer (SAP). The absorbent component is desirably a water-swellable, water-insoluble polymer.

The fibrous material releases the activating agent upon stimulation with an activator, which desirably is the liquid that is to be absorbed by the superabsorbent. This liquid will generally be an aqueous liquid such as urine or another bodily fluid. The fibrous material desirably releases the activating agent over a period of time, desirably at a controlled rate.

The absorbency of the SAP is greater than the absorbency of the fibrous material or the absorbent material separately. As the activating agent is released from the fibrous material at a controlled rate, the absorbent polymer gains the functional characteristics of a hydrophilic SAP over a period of time. In one embodiment, the SAP is a slow SAP.

In one aspect, therefore, the present invention is absorbent structures that form a superabsorbent composition in situ that absorbs liquid and is able to absorb a relatively large quantity of the liquid.

In one embodiment, the polymer is polyacrylic acid gel, and the fibrous material carries a basic activating agent, such as sodium bicarbonate, sodium carbonate or a mixture thereof.

In another aspect, the invention is a fibrous material that contains an activating agent that it can release over a period of time, desirably at a controlled rate. The fibrous material can be combined with an absorbent, wherein release of the activating agent causes the absorbent to act as an SAP. In one embodiment, the fibrous material is a cellulosic fiber having sodium bicarbonate, sodium carbonate, or a mixture thereof incorporated therein.

In another aspect, the invention is methods for forming a superabsorbent polymer in situ.

In one embodiment, the methods include providing a fibrous material containing an activating agent that the fibrous material releases upon contact with the activating liquid and providing a water-swellable, water-insoluble polymer that will form a superabsorbent upon contact with the activating agent. When the activating liquid is brought into contact with the fibrous material, the activating agent is released, whereupon the activating agent causes the water-swellable, water-insoluble polymer to form a superabsorbent.

In another aspect, the invention is a disposable absorbent product that includes an absorbent structure of the present invention. In one embodiment, a disposable absorbent product includes a liquid-permeable topsheet, a backsheet attached to the topsheet, and an absorbent structure of the present invention positioned between the topsheet and the backsheet.

DETAILED DESCRIPTION OF THE INVENTION

An absorbent structure is disclosed that forms a superabsorbent material that exhibits a relatively high total liquid absorption capacity. In one embodiment, the SAP absorbs liquid at a relatively slow liquid absorbing rate. The absorbent structure includes at least two components: an absorbent material and a fibrous material that releases an activating agent that causes the absorbent material to become a superabsorbent polymer. One of the components is acidic and one is basic, and the absorbent structure forms an absorbent composition that exhibits significant and unexpected improvements in its absorbent properties, including improved total liquid absorption as well as, optionally, a slower liquid absorbing rate, as compared to the properties exhibited by either of the components alone.

I. Definitions

As used herein, an "acidic" material refers to a material that may act as an electron acceptor.

As used herein, a "basic" material refers to a material that may act as an electron donor.

As used herein, the term "cellulosic" or "cellulose" is meant to include any material having cellulose as a major constituent, and specifically, comprising at least 50 percent by weight cellulose or a cellulose derivative. Thus, the term includes cotton, typical wood pulps, cellulose acetate, cellulose triacetate, rayon, thermomechanical wood pulp, chemical wood pulp, debonded chemical wood pulp, milkweed, and the like.

As used herein, the term "water-swellable, water-insoluble" refers to a material that, when exposed to an excess of water, swells to its equilibrium volume but does not dissolve into the solution. As such, a water-swellable, water-insoluble material generally retains its original identity or physical structure, but in a highly expanded state, during the absorption of the water and, thus, must have sufficient physical integrity to resist flow and fusion with neighboring particles. As used herein, a material will be considered to be water soluble when it substantially dissolves in excess water to form a solution, thereby losing its initial, typically particulate, form and becoming essentially molecularly dispersed throughout the water solution. As a general rule, a water-soluble material will be free from a substantial degree of crosslinking, as crosslinking tends to render a material water-insoluble.

The term "superabsorbent" as used herein refers to a material capable of absorbing large quantities of liquids such as water and body exudates in relation to its weight and forming hydrogels thereby. Superabsorbents are often capable of retaining absorbed fluids under moderate pressure. Hydrogels are also referred to as hydrocolloids and gels.

The term "slow, superabsorbent" as used herein refers to a superabsorbent having an absorption time index of at least 5 minutes and desirably more than 10 minutes. The absorption time index is defined as the time for a SAP to swell to 60% of its free swelling capacity.

"Papermaking fibers," as used herein, include all known cellulosic fibers or fiber mixes comprising cellulosic fibers. Fibers suitable for making the webs of this invention comprise any natural or synthetic cellulosic fibers including, but not limited to: nonwoody fibers, such as cotton fibers and cotton derivatives, abaca, kenaf, sabai grass, flax, esparto grass, straw, jute hemp, bagasse, milkweed floss fibers, and pineapple leaf fibers; and woody fibers such as those obtained from deciduous and coniferous trees, including softwood fibers, such as northern and southern softwood kraft fibers; hardwood fibers, such as eucalyptus, maple, birch, aspen, or the like. Wood fibers may be prepared in high-yield or low-yield forms and may be pulped in any known method, include kraft, sulfite, groundwood, thermomechanical pulp (TMP), chemithermomechanical pulp (CTMP) and bleached chemithermomechanical pulp (BCTMP). High brightness pulps, including chemically bleached pulps, are especially desired for tissue making, but unbleached or semi-bleached pulps may also be used. Recycled fibers are included within the scope of the present invention. Any known pulping and bleaching methods may be used.

Synthetic cellulose fiber types include rayon in all its varieties and other fibers derived from viscose or chemically modified cellulose. Chemically treated natural cellulosic fibers may be used such as mercerized pulps, chemically stiffened or crosslinked fibers, sulfonated fibers, and the like. Suitable papermaking fibers may also include recycled fibers, virgin fibers, or mixes thereof.

As used herein, "mercerization" is meant to refer to a process wherein cellulosic fibers are treated under suitable conditions to convert the cellulose from its native form, sometimes referred to as cellulose I, into another crystalline form, sometimes referred to as cellulose II. Because the chemically treated or mercerized cellulose is less crystalline and more amorphous, the chemically treated or mercerized cellulose is generally more accessible for further treatment with additional reagents. Known test methods exist for quantifying the chemical treatment, such as the degree of mercerization that occurs, of cellulosic fibers.

II. Compositions

The absorbent compositions of the present invention generally include at least two components. The first component is a water-swellable, water-insoluble polymer. As used in the absorbent structure of the present invention, the water-swellable, water-insoluble polymer to a large extent needs to provide the absorbent composition with its liquid-absorbing capacity. As such, the water-swellable, water-insoluble polymer needs to be able to be effective to provide a desired amount of liquid-absorbing capacity to the absorbent composition. The second component is a fibrous material having incorporated therein an activating agent that it releases over a period of time. The activating agent acts on the water-swellable, water-insoluble polymer to form a superabsorbent polymer (SAP). The activating agent is desirably a neutralizing agent that neutralizes the acidic or basic absorbent material, causing it to become a SAP.

By "releases the activating agent" it is meant herein that the fibrous material releases all or a portion of the compound that is incorporated into or onto the fibrous material. Only a portion of the incorporated compound may be released and all or a portion of the released compound may act upon the water-swellable water-insoluble polymer to cause it to become a super absorbent polymer.

The SAP formed by the absorbent structure suitably has the ability to absorb a liquid, herein referred to as Gel Capacity. The method by which the Gel Capacity is determined is set forth below. As a general rule, it is desired that the SAP of the present invention has a Gel Capacity value, for a load of about 0.01 psi, of at least about 10, more desirably of at least about 20, even more desirably of at least about 25, most desirably of at least about 35, and up to about 200 grams per gram. The gel capacity desirably ranges from about 30 to about 45.

A. The Polymer

One property of the water-swellable, water-insoluble polymer that is relevant to its effectiveness in providing a desired amount of liquid-absorbing capacity to the absorbent composition is its molecular weight. In general, a water-swellable, water-insoluble polymer with a higher molecular weight will exhibit a higher liquid-absorbing capacity as compared to a water-swellable, water-insoluble polymer with a lower molecular weight.

The water-swellable, water-insoluble polymer useful in the absorbent composition may generally have a wide range of molecular weights. A water-swellable, water-insoluble polymer having a relatively high molecular weight is often beneficial for use in the present invention. Nonetheless, polymers having a wide range of molecular weights are generally suitable for use in the present invention. Water-swellable, water-insoluble polymers suitable for use in the present invention will beneficially have a weight average molecular weight greater than about 100,000, more beneficially greater than about 200,000, suitably greater than about 500,000, more suitably greater than about 1,000,000, and up to about 10,000,000. Methods for determining the molecular weight of a polymer are generally well known in the art.

It is sometimes more convenient to express the molecular weight of a polymer in terms of its viscosity in a 1.0 weight percent aqueous solution at 25° C. Polymers suitable for use in the present invention will suitably have a viscosity in a 1.0 weight percent aqueous solution at 25° C. of from about 100 centipoise (100 mPa·s) to about 80,000 centipoise (80,000 mPa·s), more suitably from about 500 centipoise (500 mPa·s) to about 80,000 centipoise (80,000 mPa·s), and most suitably from about 1,000 centipoise (1,000 mpa·s) to about 80,000 centipoise (80,000 mPa·s).

The water-swellable, water-insoluble polymer useful in the absorbent composition will generally be crosslinked. The amount of crosslinking should generally be above a minimum amount sufficient to make the polymer water-insoluble but also below some maximum amount so as to allow the polymer to be sufficiently water swellable so that the water-swellable, water-insoluble polymer absorbs a desired amount of liquid.

Crosslinking of the polymer may generally be achieved by either of two different types of crosslinking agents. The first type of crosslinking agent is a polymerizable crosslinking agent. Suitable polymerizable crosslinking agents are generally reactive to the monomer or monomers used to prepare the polymer and, thus, generally comprise at least two functional groups that are capable of reacting with the monomers. Examples of suitable polymerizable crosslinking agents include ethylenically unsaturated monomers, such as N,N'-methylene bis-acrylamide, for free radical polymerization, and polyamines or polyols for condensation polymerization.

The second type of crosslinking agent is a latent crosslinking agent. Latent crosslinking agents generally do not take part in the overall polymerization process but, instead, are reactive to the polymer at a later point in time when a proper crosslinking condition is provided. Suitable post treatment conditions include using heat treatment, such as a temperature above about 60° C., exposure to ultraviolet light, exposure to microwaves, steam or high humidity treatment, high pressure treatment, or treatment with an organic solvent.

Latent crosslinking agents suitable for use in the present invention are generally water soluble. A suitable latent crosslinking agent is an organic compound having at least two functional groups or functionalities capable of reacting with any carboxyl, carboxylic, amino, or hydroxyl groups on the polymer. Examples of suitable latent crosslinking agents include, but are not limited to, diamines, polyamines, diols, polyols, polycarboxylic acids, and polyoxides. Another suitable latent crosslinking agent comprises a metal ion with more than two positive charges, such as $Al^{3+}$, $Fe^{3+}$, $Ce^{3+}$; $Ce^{4+}$, $Ti^{4+}$, $Zr^{4+}$, and $Cr^{3+}$.

When the polymer is a cationic polymer, a suitable crosslinking agent is a polyanionic material such as sodium polyacrylate, carboxymethyl cellulose, or polyphosphate.

The water-swellable, water-insoluble polymer useful in the absorbent composition will either be acidic or basic in nature. In general, weakly acidic water-swellable, water-insoluble polymers will provide slower superabsorbents whereas strongly acidic polymers will provide superabsorbents having faster action. Accordingly, the polymer can be chosen in part based upon the desired speed of absorbency of the formed superabsorbent polymer.

Suitable acidic water-swellable, water-insoluble polymers will include functional groups that are capable of acting as acids. Such functional groups include, but are not limited to, carboxyl groups, sulfate groups, sulfite groups, and phosphate groups. Suitably, the functional groups are carboxyl groups. Generally, the functional groups are attached to a crosslinked base polymer. Suitable base polymers include polyacrylamides, polyvinyl alcohols, ethylene maleic anhydride copolymer, polyvinylethers, polyacrylic acids, polyvinylpyrrolidones, polyvinylmorpholines, and copolymers thereof. Natural based polysaccharide polymers may also be used and include carboxymethyl celluloses, carboxymethyl starches, hydroxypropyl celluloses, algins, alginates, carrageenans, acrylic grafted starches, acrylic grafted celluloses, and copolymers thereof. Synthetic polypeptides can also be used such as polyaspartic acid and polyglutamic acid. Copolymers and mixtures of the above can also be used.

The acidic, water-swellable, water-insoluble polymer generally needs to be in its free acid form. In general, it is desired that the acidic, water-swellable, water-insoluble polymer beneficially have at least about 50 molar percent, more beneficially at least about 70 molar percent, suitably at least about 80 molar percent, more suitably at least about 90 molar percent, and most suitably substantially about 100 molar percent of its acidic functional groups in free acid form. Alternatively, the acidic, water-swellable, water-insoluble polymer should not be substantially neutralized when used in the absorbent composition of the present invention. In general, it is desired that the acidic, water-swellable, water-insoluble polymer have a degree of neutralization of its acidic functional groups that is beneficially less than about 50 molar percent, more beneficially less than about 30 molar percent, suitably less than about 20 molar percent, more suitably less than about 10 molar percent, and most suitably substantially about 0 molar percent.

Desired acidic water-swellable, water-insoluble polymers useful in the invention are polyacrylic acid, ethylene maleic anhydride copolymer, acrylic acid grafted starch, acrylic acid grafted cellulose, carboxymethyl cellulose, and polyacrylamide methylpropane sulfonic acid. Most desired acidic water-swellable, water-insoluble polymers include polyacrylic acid, polyacrylamide methylpropane sulfonic acid, and acrylic acid grafted starch.

In one embodiment of the invention, where the desire is to make slow superabsorbents, the acidic, water-swellable, water-insoluble polymers used in the absorbent composition will be weakly acidic in nature. Such polymers will beneficially have a $pK_a$ between about 2 to about 12, more beneficially between about 2 to about 10, and most desirably between about 3 to about 6. It may sometimes be more convenient to measure the pH of the monomer or monomers used to prepare a polymer. Although the pH of the monomer or monomers and the polymer prepared from such monomers may not be identical, such pH values should be substantially similar. As such, acidic, water-swellable, water-insoluble polymers useful in the absorbent composition will be prepared from monomers that beneficially have a $pK_a$ between about 2 to about 12, more beneficially between about 2 to about 10, and most desirably between about 3 to about 6. If a polymer is prepared from two or more monomers, each of the monomers used should beneficially have a $pK_a$ between about 2 to about 12, more beneficially between about 2 to about 10, and most desirably between about 3 to about 6, although insubstantial amounts of monomers having a $pK_a$ less than about 2 or greater than about 12 may be used as long as such monomers do not negatively affect the desired properties of the water-swellable, water-insoluble polymer useful herein.

The $pK_a$ of an acid represents the extent of dissociation of or, in other words, the strength of the acid and is intended herein to be measured at the conditions, such as at a specific temperature, under which the water-swellable, water-insoluble polymer is being used. Suitably, the $pK_a$ is measured at about 25 ° C. In general, the weaker the acid, the higher the $pK_a$ value will be. The $pK_a$ values for many acids at various temperatures are well known and may be found in any of many available references, such as in the CRC Handbook of Chemistry & Physics, 75th Edition, edited by David R. Lide, CRC Press (1994).

Suitable basic, water-swellable, water-insoluble polymers will include functional groups that are capable of acting as bases. Such functional groups include, but are not limited to, primary, secondary, or tertiary amino groups, imino groups, imido groups, and amido groups. Suitably the functional groups are amino groups. Generally, the functional groups are attached to a crosslinked base polymer. Suitable base polymers include polyamines, polyethyleneimines, polyacrylamides, polydiallyl dimethyl ammonium hydroxide, and polyquaternary ammoniums. Natural based polysaccharide polymers may also be used and include chitin and chitosan. Synthetic polypeptides can also be used such as polyasparagines, polyglutamines, polylysines, and polyarginines. Mixtures and copolymers of the foregoing can also be used.

The basic, water-swellable, water-insoluble polymer generally needs to be in its free base form. In general, it is desired that the basic, water-swellable, water-insoluble polymer beneficially have at least about 50 molar percent, more beneficially at least about 70 molar percent, suitably at least about 80 molar percent, more suitably at least about 90 molar percent, and most suitably substantially about 100 molar percent of its basic, functional groups in free base form. Alternatively, the basic, water-swellable, water-insoluble polymer should not be substantially neutralized when used in the absorbent composition of the present invention. In general, it is desired that the basic, water-swellable, water-insoluble polymer have a degree of neutralization of its basic functional groups that is beneficially less than about 50 molar percent, more beneficially less than about 30 molar percent, suitably less than about 20 molar percent, more suitably less than about 10 molar percent, and most suitably substantially about 0 molar percent.

Desired basic water-swellable, water-insoluble polymers useful in the invention include chitosan, quaternary ammoniums, polyvinylamine, polyethylene imine, and polydialkylaminoalkyl methacrylamide. Most desired basic water-swellable, water-insoluble polymers useful in the invention include quaternary ammoniums, polyvinylamine, and polyethylene imine.

In one embodiment of the invention, where the desire is to make slow superabsorbents, the basic, water-swellable, water-insoluble polymer will be weakly basic in nature. Such polymers will beneficially have a $pK_b$ between about 2 to about 12, more beneficially between about 2 to about 10, and suitably between about 3 to about 6. It may sometimes be more convenient to measure the pH of the monomer or monomers used to prepare a polymer. Although the pH of the monomer or monomers and the polymer prepared from such monomer or monomers may not be identical, such pH values should be substantially similar. As such, basic, water-swellable, water-insoluble polymers useful in the absorbent composition will be prepared from monomers that beneficially have a $pK_b$ between about 2 to about 12, more beneficially between about 2 to about 10, and suitably between about 3 to about 6. If a polymer is prepared from two or more monomers, each of the monomers used should beneficially have a $pK_b$ between about 2 to about 12, more beneficially between about 2 to about 10, and suitably between about 3 to about 6, although insubstantial amounts of monomers having a $pK_b$ less than about 2 or greater than about 12 may be used as long as such monomers do not negatively affect the desired properties of the water-swellable, water-insoluble polymer useful herein.

The $pK_b$ of a base represents the extent of dissociation of or, in other words, the strength of the base and is intended herein to be measured at the conditions, such as at a specific temperature, under which the water-swellable, water-insoluble polymer is being used. Suitably, the $pK_b$ is measured at about 25° C. In general, the weaker the base, the higher the $pK_b$ value will be. The $pK_b$ values for bases at various temperatures are well known and may be found in any of many available references, such as in the CRC Handbook of Chemistry & Physics, 75th Edition, edited by David R. Lide, CRC Press (1994).

The acidic or basic water-swellable, water-insoluble polymer may generally be used in the absorbent composition in a variety of forms. Examples of forms that the acidic or basic water-swellable, water-insoluble polymer may take include particles, flakes, fibers, films, and nonwoven structures. When the absorbent structure is used in absorbent disposable products, it is generally desired that the acidic or basic water-swellable, water-insoluble polymer be in the form of discrete particles, fibers, or flakes. When in the form of a particle, it is generally desired that the particle have a maximum cross-sectional dimension beneficially within the range from about 50 micrometers to about 2,000 micrometers, suitably within the range from about 100 micrometers to about 1,000 micrometers, and more suitably within the range from about 300 micrometers to about 600 micrometers.

B. The Fibrous Material

The fibrous material is desirably a fibrous matrix having a form such as a fibrous network, which is, generally, a random plurality of fibers that can, optionally, be joined together with a binder. The fibrous material can alternatively have the form of a batt of comminuted wood pulp fluff, a tissue layer, a hydroentangled pulp sheet, a woven sheet, a nonwoven sheet, a tow, or a mechanically softened pulp sheet. In desired embodiments, the fibrous material is similar to the fibrous material that otherwise would be used in the absorbent article.

Any papermaking fibers, as previously defined, or mixtures thereof may be used that can retain the activating agent and release it, desirably in a controlled fashion over a period of time. Because of commercial availability, softwood and hardwood fibers are especially desired. In one embodiment, the fibers may be predominantly hardwood, such as at least 50% hardwood or about 60% hardwood or greater or about 80% hardwood or greater or substantially 100% hardwood. Higher hardwood contents are desired for high opacity and softness, whereas higher softwood content is desirable for strength. In another embodiment, the fibers may be predominantly softwood, such as at least 50% softwood or about 60% softwood or greater or about 80% softwood or greater or substantially 100% softwood.

The fibrous material may be formed from a single layer or multiple layers. In the case of multiple layers, the layers are generally positioned in a juxtaposed or surface-to-surface relationship and all or a portion of the layers may be bound to adjacent layers. The fibrous material may also be formed from a plurality of separate fibrous webs wherein the separate fibrous webs may be formed from single or multiple layers.

To achieve good softness and opacity, it is desirable that the fibrous component comprise substantial amounts of hardwood. For good strength, substantial amounts of softwood are desired. Both strength and softness are often achieved through layered tissues, such as those produced from stratified headboxes wherein at least one layer delivered by the headbox comprises softwood fibers while another layer comprises hardwood or other fiber types. Layered tissue structures produced by any means known in the art are within the scope of the present invention, including those disclosed by Edwards et al. in U.S. Pat. No. 5,494,554.

The fibrous material contains the activating agent and can release the activating agent, desirably in a controlled manner. By controlled manner is meant at an approximately constant rate over a period of time. The fibrous material desirably releases the activating agent upon contact with an activator, which is usually an insult liquid which is to be absorbed by the superabsorbent. The activating agent can be retained on the fibrous material by a number of means. For example, the activating agent can be retained by water labile bonds, such as ionic bonds or water hydrolyzable covalent bonds. The activating agent can also be retained by physical means, such as encapsulation or physical entrapment.

The rate of release of the activating agent from the fibrous material is controlled by several factors. One factor is the concentration of the activating agent and the nature of the activating agent such as its molecular weight, charge, and solubility. Another factor is the type and strength of the bond or interaction between the agent and the fiber. For example, an activating agent that is carried within the structure of the fibrous material will likely be released more slowly than an activating agent carried on the matrix surface.

C. The Activating Agent

If the water-swellable, water-insoluble polymer is acidic, the activating agent will be basic. Alternatively, if the water-swellable, water-insoluble polymer is basic, the activating agent will be acidic. Examples of basic activating agents are carbonates and bicarbonates such as sodium bicarbonate and sodium carbonate, polyamines, polyimines, polyamides, polyquaternary ammoniums, chitins, chitosans, polyasparagines, polylysines, polyarginines, aliphatic amines, aromatic amines, imines, amides, metallic oxides, hydroxides such as sodium hydroxide, potassium hydroxide, and lithium hydroxide, salts, ammonia, and mixtures and copolymers thereof. Desired basic activating agents are sodium bicarbonate, sodium carbonate, potassium carbonate, and potassium bicarbonate.

Examples of acidic activating agents are polyacrylic acid, polymaleic acid, carboxymethyl cellulose, alginic acid, polyaspartic acid, polyglutamic acid, citric acid, glutamic acid, aspartic acid, inorganic acid, salts, isosaccharinic acid, tartaric acid, oxalic acid, malonic acid, glucuronic acid and mixtures and copolymers thereof. Desired acidic activating agents are citric acid, glutamic acid, aspartic acid, ammonium chloride, and calcium chloride.

The activating agent is included in the fibrous material at about 5 to 80 weight percent, desirably at about 10 to 50 weight percent, and most desirably at about 20 to 40 weight percent.

The activating agent and the polymer should be present in the absorbent structure in an acid to base ratio from about 1:5 to 5:1, desirably from about 1:2 to 2:1, and most desirably at about a 1:1 acid to base ratio.

When the activating agent is basic, the pH of the fibrous material ranges from about 7.5 to 14, and is desirably about 7.5 to 9.0. When the activating agent is acidic, the pH of the fibrous material ranges from about 0 to 6.5, and is desirably about 4 to 6.5.

D. Buffering Agent

Optionally, a buffering agent can be included to maintain the pH of the surface of the products. Buffering agents that can be used include aspartic acid, ascorbic acid, chloroacetic acid, β-chlorobutyric acid, cis-cinnamic acid, citric acid, fumaric acid, glutaramic acid, glutaric acid, itaconic acid, lactic acid, malic acid, malonic acid, o-phthalic acid, succinic acid, α-tartaric acid, and phosphoric acid, α-alanine, allantoin, cysteine, cystine, dimethylglycine, histidine, glycine, chitosan, N-(2-acetamido)-2-iminodiacetic acid, tris(hydroxymethyl) aminomethane, theobromine, and tyrosine.

While the principal components of the absorbent composition of the present invention have been described in the foregoing, such absorbent composition is not limited thereto and can include other components not adversely effecting the absorbent composition having the desired absorbent properties. Exemplary materials which could be used as additional components include, without limitation, pigments, antioxidants, stabilizers, surfactants, waxes, flow promoters, solid solvents, particulates, and materials added to enhance processability of the absorbent composition.

II. Methods of Making the Absorbent Structures

The water-swellable water-insoluble polymers are commercially available or can be made by methods well known in the art. The fibrous material can also be made by methods known to those skilled in the art. The activating agent may be incorporated into or onto the fibrous material during or after the formation of the general form of the fibrous material. A fibrous material useful in the present invention may be formed by an air-laying process or a wet-laid process, or by essentially any other process known to those skilled in the art for forming a fibrous material.

In general, the activating agent is incorporated into or onto the fibrous material by a process which involves reversibly bonding the agent to the material, reversibly encapsulating the agent into the material, or reversibly physically entrapping the agent in the fibrous material. Accordingly, the interaction between the activating agent and the fibrous material can be an ionic interaction, a labile covalent interaction, or a physical interaction. Combinations of these types of processes and interactions can also be used.

In one embodiment, the process involves dispersing the fibrous material into a liquid phase that includes at least one component that can loosen the fibrous material's supermolecular structure, such as sodium hydroxide or potassium hydroxide. This component may be retained by the fibrous material or may be washed away. The activating agent or a compound that will form the agent is then added to the dispersion. The agent or compound is desirably soluble in the liquid phase. The liquid phase is then removed so that the cellulosic fiber encapsulates, or retains, the activating agent inside its supermolecular structure.

In one embodiment, the activated agent containing fibrous material is prepared using mercerized cellulosic fibrous material. Any of a number of methods of mercerization can be used, a desired method is that disclosed in U.S. Pat. No. 5,858,021 to Sun et al. That method involves preparation of a first mixture of cellulosic fibers and water, desirably at a consistency of between about 27 to 100 weight percent, most desirably between about 40 and 80 weight percent. An alkali metal hydroxide is added to the first mixture to make a second mixture. The alkali metal hydroxide is desirably sodium hydroxide, potassium hydroxide, lithium hydroxide, or mixtures thereof. Tha alkali metal hydroxide is desirably added at an amount of between about 5 to 55 weight peercent of the second mixture, more desirably between about 13 to 50 weight percent, based upon the total weight of alkali metal hydroxide and water in the mixture. The second mixture is homogenized and, desirably, heated to about 60° C. to 80° C. to effectively mercerize the fibers.

The mercerized fibrous material is then quickly rinsed, but not washed as is standard after mercerization processes. The fiber is exposed to carbon dioxide and a mixture of sodium bicarbonate and sodium carbonate is formed and embedded inside the fiber wall, the lumen, and a limited amount will be retained on the fiber surface. This method provides an advantage in terms of preparation of the fiber and the absorbent material in that the fiber does not have to be washed after NaOH treatment, as is usually done in mercerization processes.

Absorbent structures can be made in the same way as absorbent structures without the activating agent treated fibrous material.

III. Methods of Using the Absorbent Structures

The absorbent structures of the present invention are suitable for use in disposable absorbent products such as personal care products, such as diapers, training pants, baby wipes, feminine care products, adult incontinent products; and medical products, such as wound dressings, surgical capes, and drapes. When the absorbent structure of the present invention is intended for use in disposable absorbent products, it is typically desired that the resultant superabsorbent composition have a generally neutral or slightly acidic character. For such a particular use, it is generally desired that the molar ratio of acidic or basic water-swellable, water-insoluble polymer to basic or acidic activating agent be about 1:1.

In one embodiment of the present invention, a disposable absorbent product is provided, which includes a liquid-permeable topsheet, a backsheet attached to the topsheet, and an absorbent structure of the invention positioned between the topsheet and the backsheet.

Disposable absorbent products, according to all aspects of the present invention, are generally subjected during use to multiple insults of a body liquid. Accordingly, the disposable absorbent products are desirably capable of absorbing multiple insults of body liquids in quantities to which the absorbent products and structures will be exposed during use. The insults are generally separated from one another by a period of time.

Those skilled in the art will recognize materials suitable for use as the topsheet and backsheet. Exemplary of materials suitable for use as the topsheet are liquid-permeable materials, such as spunbonded polypropylene or polyethylene having a basis weight of from about 15 to about 25 grams per square meter. Exemplary of materials suitable for use as the backsheet are liquid-impervious materials, such as polyolefin films, as well as vapor-pervious materials, such as microporous polyolefin films.

The absorbent structure of the present invention should be present in an amount effective to form superabsorbent composition effective to result in the absorption of a desired amount of liquid.

The invention is further illustrated by the following examples, which are not to be construed in any way as imposing limitations upon the scope thereof. On the contrary, it is to be clearly understood that resort may be had to various other embodiments, modifications, and equivalents thereof, which, after reading the description herein, may suggest themselves to those skilled in the art without departing from the spirit of the present invention.

EXAMPLES

Testing Method for Gel Capacity

The Flooded Absorbency Under Zero Load (FAUZL) test method was used to determine Gel Capacity. This test is designed to measure the saline absorption rate of particulate superabsorbent polymer (SAP). The test measures the amount of saline absorbed by 0.160 grams of superabsorbent polymer (starting either dry or presaturated) within a period of time, when it is confined within a 5.07 cm$^2$ area under a determined nominal pressure of 0.01 psi (0.069 KPa).

In this test, a certain amount of SAP is placed into a one (1) inch inside diameter plastic cylinder having a 100 mesh stainless steel screen affixed to the cylinder bottom. The operator should avoid allowing the SAP to contact the sides of the cylinder because granules may adhere and the operator should gently tap the cylinder until the granules are evenly distributed on the screen.

A 4.4 gram plastic piston disk having a 0.995 inch (25.27 mm) diameter is inserted into the cylinder. The cylinder group is weighed. This weight is the "cylinder group dry weight."

A saline disk container (inner diameter of 2.125 inch (53.98 mm), inner depth of 0.5 inch (12.70 mm)) is filled with 20 gram blood bank saline (0.9% NaCl solution) and a certain amount of the treated pulp for a setting period of time.

The cylinder group is placed in the saline disk. After the setting time, the cylinder is removed from the saline and the cylinder is blotted dry on ten layers of Hi-Dri Double Roll brand paper towel. The blotting is continued by moving the cylinder to the area (about 5 seconds) with dry paper towel until there is no fluid mark visible on the paper towel.

The cylinder group is now weighed. This weight is the "cylinder group wet weight." The difference between the cylinder group wet weight and the cylinder group dry weight is the total amount of fluid absorbed by the absorbent material and is used to calculate Gel Capacity. The Gel Capacity is the grams of liquid absorbed divided by the grams of gel.

Example 1

Polyacrylic Acid Absorbent and Sodium Carbonate Activating Agent

Preparation of Polyacrylic Acid (PAA) Gel 27 grams of acrylic acid, 0.05 gram of potassium persulfate ($K_2S_2O_8$) and 0.108 gram N,N'-methylene bisacrylamide, all available from Aldrich Chemical Company, were added to 175 grams of distilled water in a 500 ml flask, and fat, mixed at room temperature to form a completely dissolved solution. The flask was then immersed into water bath at 60° C. for at least three hours and shaken continuously. The resulting PAA gel formed was cut and dried in a ventilated oven at 80° C. for 10 hours. The completely dried polymer was ground into particulate by a commercial blender from Warring (Model 34BL97) and sieved into 300 to 600 µm particle size range.

Treatment of Pulp With Activating Agent 600 grams of oven dried CR-54, a fully bleached Southern pine kraft pulp produced by U.S. Alliance Coosa Pines Corporation, Alabama (1714 grams at 35% solids) and 886 ml water were mixed to form a pulp. 480 grams of NaOH dissolved in 400 ml of water was added to the pulp and the combination was mixed for 20 minutes at room temperature. After mixing, the excess liquid was removed using vacuum, and the mixture was rediluted with an additional 1000 ml of water. It was then dewatered again. The pulp was broken up (shredded) and placed in a large plastic pail. Carbon dioxide was introduced to the pail with Tygon tubing, while mixing the pulp from the bottom to allow for maximum exposure of the pulp to the gas. After mixing for 2 hours, the pail was sealed to equilibrate for an additional sixty (60) hours. The pH was between 7 and 8. The pulp was manually mixed and dried overnight in a 105° C. oven, yielding 1110 grams (185%).

Sodium Content Analysis

The amount of sodium in the treated CR54 bicarbonate pulp was determined to be about 16.46% by weight. Triplicate portions of the material were ashed, treated with sulfuric acid, and heated to 850° C. to convert the elemental sodium to sodium sulfate and remove any extraneous carbonaceous material. The amount of sodium present was determined by calculation from the weight of sodium sulfate formed. The amount of sodium present was 16.5% which translates into 36% sodium in the carbonate/ bicarbonate form. Since $Na_2CO_3$ contains 43.4% sodium, and $NaHCO_3$ contains 27.4% sodium, a portion of the sodium is present as $Na_2CO_3$ and a portion is present as $NaHCO_3$.

Gel Capacity

The gel capacity of the PAA prepared as above and combined with the treated fiber was measured by the Flooded Absorbency Under Zero Load (FAUZL) test method. 0.300±0.002 gram of polyacrylic acid (PAA) was used. Various amounts of $NaHCO_3$ treated pulp was immersed and stirred with 20 grams of saline and the pH value of the solution was measured by pH indicator paper with 0.5 increment. The cylinder containing the PAA was placed in the pulp solution. After 60 minutes, the Gel Capacity of the formed SAP was measured. The pH value of the solution was measured again after the SAP was taken out of the solution. The results are shown in Table 1.

TABLE 1

Gel Capacity

| PAA (grams) | 0.30 | 0.30 | 0.30 | 0.30 | 0.30 |
|---|---|---|---|---|---|
| treated pulp (grams) | 0 | 0.30 | 0.60 | 1.50 | 3.0 |
| pH pulp solution | 5.5 | 11 | 12 | 12 | 12 |
| Gel (grams) | 2.54 | 11.28 | 14.23 | 12.34 | 10.06 |
| Gel Capacity (g/g) | 7.5 | 36.6 | 45.3 | 42.1 | 32.5 |
| pH gel solution | 4.5 | 11 | 11 | 11 | 11 |

The pulp was found to be very effective at neutralizing the PAA. The final gel capacity ranged from about 32 g/g to about 45 g/g which was very satisfactory.

Example 2

Treatment of Fibrous Material With Different Add-On Amounts of NaOH 1800 grams of oven dried fully bleached southern softwood (CR54) was pulped, mixed to disperse the nits, and then dewatered to a consistency of 44%. To prepare three add-on levels of sodium bicarbonate/sodium carbonate loaded fibers, 960 gram, 1920 gram and 2880 gram of 50% (wt/wt) NaOH solution was added to the pulp in each individual mixer, respectively. Water was added so that in each mixer the total amount of water was 900 gram (or the pulp consistency was about 16.7%). The combination was mixed for 20 minutes at room temperature (23° C.). After mixing, the pulp was transferred to the centrifuge and given a gentle wash. The slurry was then dewatered to about 34% consistency and broken up in the fluffer. The pulp was placed in the mixer and tumbled for 24 hours under atmospheric pressure in the presence of carbon dioxide. The pH of the pulp solution was found to be 8.2 to 8.5 for each sample. The fiber was then fiberized. To determine the amount of sodium bicarbonate in fibers, the samples were extracted three times in distilled water with orbital shaking for 15 minutes. The fibers were filtered through a glass fiber filter in a gooch crucible. An aliquot of the extract was titrated with hydrochloric acid.

The Gel Capacity of polyacrylic acid (PAA), prepared as above, combined with the treated fibers of this example was measured by the Flooded Absorbency Under Zero Load (FAUZL) test method described above. 0.160±0.002 gram PAA was used. One gram of $NaHCO_3$ encapsulated treated pulp with various sodium bicarbonate weight percentages was stirred with 20 grams of saline (0.9% NaCl). After stirring the pulp in saline about 4 minutes, the test cylinder was placed in the pulp solution. The sample was tested for $NaHCO_3$ and the test results are shown in Table 2. BC/(BC+ Pulp) represents the bicarbonate content in the treated fiber determined by the extraction/ titration method described above.

TABLE 2

Gel Capacity

| Dry PAA weight (grams) | 0.160 | 0.160 | 0.160 | 0.160 |
|---|---|---|---|---|
| untreated fiber (grams) | 1.0 | 0 | 0 | 0 |
| treated fiber (grams) | 0 | 1.0 | 1.0 | 1.0 |
| BC/(BC + Pulp) % | 0 | 14.5 | 26.5 | 50.2 |
| Gel Capacity in 3 hours (gram/gram) | 5.0 | 36.5 | 43.3 | 42.2 |
| Gel capacity in 24 hours (gram/gram) | 5.0 | 42.5 | 43.2 | 43.2 |

Example 3

Treatment of Fibrous Material With Different Add-On Amounts of $NaHCO_3$ 1000 grams of oven dried fully bleached southern softwood (CR54) was pulped, mixed to disperse the nits, and then dewatered to a consistency of 30%. To prepare three add-on levels of sodium bicarbonate/sodium carbonate loaded fibers, 170 grams, 340 grams, and 1000 grams of $NaHCO_3$ was added to the pulp in each individual mixer, respectively. To determine the amount of sodium bicarbonate in fibers, the samples were extracted three times in distilled water with orbital shaking for 15 minutes. The fibers were filtered through a glass fiber filter in a gooch crucible. An aliquot of the extract was titrated with hydrochloric acid. The testing results were calculated as $N_aHCO_3$.

The Gel Capacity of polyacrylic acid (PAA), prepared as above, combined with the treated fibers of this example was measured by the Flooded Absorbency Under Zero Load (FAUZL) test method described above. 0.160±0.002 gram PAA was used. 1 gram of the treated fibers was stirred with 20 grams of saline (0.9% NaCl). After stirring the pulp in saline about 4 minutes, the test cylinder was placed in the pulp solution. The test results are shown in Table 3.

TABLE 3

Gel Capacity

| Dry PAA weight (grams) | 0.160 | 0.160 | 0.160 | 0.160 |
|---|---|---|---|---|
| untreated fiber (grams) | 1.0 | 0 | 0 | 0 |
| treated fiber (grams) | 0 | 1.0 | 1.0 | 1.0 |
| BC/(BC + Pulp) % | 0 | 14.4 | 22.0 | 42.8 |
| Gel Capacity in 3 hours (gram/gram) | 5.0 | 25.5 | 33.8 | 25.1 |
| Gel Capacity in 24 hours (gram/gram) | 5.0 | 34.4 | 45.0 | 36.0 |

The above description is intended to be illustrative and not restrictive. Many embodiments will be apparent to those of skill in the art upon reading the above description. The scope of the invention should, therefore, be determined not with reference to the above description, but should instead be determined with reference to the appended claims, along with the full scope of equivalents to which such claims are entitled. The disclosures of all articles and references referred to herein, including patents, patent applications and publications, are incorporated herein by reference.

What is claimed is:

1. A fibrous material comprising:
   fibers having an activating agent bonded or retained onto or within the fibers; and
   a polymer that is water-swellable and water-insoluble;
   wherein the fibers will release at least some of the activating agent upon stimulus with an activator and the activating agent will cause an increase in the capacity of at least some of the polymer to absorb water;
   further wherein the activating agent is basic and the pH of the fibers ranges from about 7.5 to 14 or wherein the activating agent is acidic and the pH of the fibers ranges from about 0 to 6.5.

2. The fibrous material of claim 1, wherein the activator is a liquid to be absorbed by the polymer.

3. The fibrous material of claim 1, wherein the fibers comprise cellulose.

4. The fibrous material of claim 1, wherein the fibers release the activating agent in a controlled manner.

5. The fibrous material of claim 4, wherein the rate of release of the activating agent from the fibers is controlled by one or more factors selected from the group consisting of the concentration of the activating agent, the nature of the activating agent, the type of interaction between the activating agent and the fibers, and the strength of the interaction between the activating agent and the fibers.

6. The fibrous material of claim 1, wherein the fibrous material has a form selected from the group consisting of a fibrous network, a batt of comminuted wood pulp fluff, a tissue layer, a hydroentangled pulp sheet, a woven sheet, a nonwoven sheet, a tow, and a mechanically softened pulp sheet.

7. The fibrous material of claim 1, wherein the fibers comprise the activating agent comprises about 5 to about 80 weight percent.

8. The fibrous material of claim 1, wherein the fibers comprise the activating agent comprises about 10 to about 50 weight percent.

9. The fibrous material of claim 1, wherein the fibers comprise the activating agent comprises about 20 to about 40 weight percent.

10. The fibrous material of claim 1, wherein the activating agent is retained on the fibers by an interaction selected from the group consisting of ionic bonds, water labile covalent bonds, encapsulation, and physical entrapment.

11. The fibrous material of claim 1, wherein the activating agent is selected from the group consisting of sodium carbonate, sodium bicarbonate, polyamines, polyimines, polyamides, polyquatemary ammoniums, chitins, chitosans, polyasparagines, polylysines, polyarginines, aliphatic amines, aromatic amines, imines, amides, metallic oxides, hydroxides, salts, ammonia, sodium hydroxide, potassium hydroxide, polyacrylic acid, polymaleic acid, carboxymethyl cellulose, alginic acid, polyaspartic acid, polyglutamic acid, citric acid, glutamic acid, aspartic acid, inorganic acid, salts, isosaccharinic acid, tartaric acid, oxalic acid, malonic acid, glucuronic acid, and mixtures and copolymers thereof.

12. The fibrous material of claim 1, wherein the polymer is acidic and the activating agent is basic.

13. The fibrous material of claim 1, wherein the polymer is basic and the activating agent is acidic.

14. The fibrous material of claim 1, wherein the polymer comprises polyacrylic acid and the activating agent is selected from the group of sodium bicarbonate, sodium carbonate, and mixtures thereof.

15. The fibrous material of claim 1, wherein the activating agent is basic and the pH of the fibers ranges from about 7.5 to 9.0.

16. The fibrous material of claim 1, wherein the activating agent is acidic and the pH of the fibers ranges from about 4 to 6.5.

17. A disposable absorbent article that includes the fibrous material of claim 1.

18. The absorbent article of claim 17, comprising a liquid-permeable topsheet, a backsheet attached to the topsheet, and the fibrous material positioned between the topsheet and the backsheet.

* * * * *